United States Patent [19]

Williams

[11] Patent Number: 5,014,374
[45] Date of Patent: May 14, 1991

[54] RESTRAINT STRETCHER

[76] Inventor: Gary R. Williams, 943 Daisy Ave., Carlsbad, Calif. 92009

[21] Appl. No.: 315,463

[22] Filed: Feb. 24, 1989

[51] Int. Cl.⁵ .................... A61F 13/00; A61G 1/00
[52] U.S. Cl. .................... 5/82 R; 128/870; 128/876
[58] Field of Search ............... 5/82 R, 82 B; 128/867, 128/870, 876

[56] References Cited

U.S. PATENT DOCUMENTS

| | | |
|---|---|---|
| 879,335 | 2/1908 | Southmayd ........................... 5/82 |
| 899,279 | 9/1908 | Wilson ................................. 5/82 |
| 2,084,305 | 6/1937 | Baun ................................. 128/876 |
| 2,279,694 | 4/1942 | Martinson . |
| 2,366,082 | 12/1944 | Baker . |
| 2,489,828 | 11/1949 | Springer . |
| 2,535,936 | 12/1950 | Langley . |
| 2,547,466 | 4/1951 | Hoder . |
| 2,675,564 | 4/1954 | Nugnes ............................. 128/870 |
| 2,788,530 | 4/1957 | Ferguson . |
| 2,899,692 | 8/1959 | Finken . |
| 3,158,875 | 12/1964 | Fletcher . |
| 3,650,523 | 3/1972 | Darby, Jr. ......................... 128/870 |
| 3,892,399 | 7/1975 | Cabansag ........................... 128/870 |
| 3,933,154 | 1/1976 | Cabansag ........................... 128/870 |
| 4,034,748 | 7/1977 | Winner . |
| 4,124,908 | 11/1978 | Burns et al. . |
| 4,186,453 | 2/1980 | Burns et al. . |
| 4,211,218 | 7/1980 | Kendrick . |
| 4,297,994 | 11/1981 | Bashow . |
| 4,394,783 | 7/1983 | Simmons . |
| 4,506,664 | 3/1985 | Brault . |
| 4,515,155 | 5/1985 | Wagemann . |
| 4,589,407 | 5/1986 | Koledin et al. . |
| 4,593,788 | 6/1986 | Miller . |
| 4,601,075 | 7/1986 | Smith . |
| 4,612,678 | 9/1986 | Fitsch ............................... 128/870 |
| 4,667,355 | 5/1987 | Nishijima . |
| 4,841,961 | 6/1989 | Burlagg et al. .................... 5/82 R |
| 4,895,173 | 1/1990 | Brault et al. ..................... 128/870 |

FOREIGN PATENT DOCUMENTS

| | | | |
|---|---|---|---|
| 116901 | 5/1943 | Australia ............................. 5/82 |
| 2157957 | 11/1985 | United Kingdom .............. 5/82 R |

OTHER PUBLICATIONS

"Guidelines for Use of the Pedi-Bacpac ™", Emergency Specialty Products, Print Date 1/88.

Primary Examiner—Eric K. Nicholson
Attorney, Agent, or Firm—Fulwider Patton Lee & Utecht

[57] ABSTRACT

A restraint stretcher comprising an envelope for receiving a rigidifying backboard, and having transverse straps for encircling the body of a patient at specific areas, the straps being mounted for longitudinal movement to fit various sizes of patient. The transverse straps and their anchorage brackets are readily individually removable for cleaning or replacement. The anchorage points can be located on the upper side of the stretcher for immobilizing smaller patients, or on the underside for immobilizing larger or adult patients. The stretcher is padded for patient comfort and includes laterally or outwardly projecting handles for transportation of the stretcher. A harness is provided to constrain the patient against longitudinal movement.

12 Claims, 2 Drawing Sheets

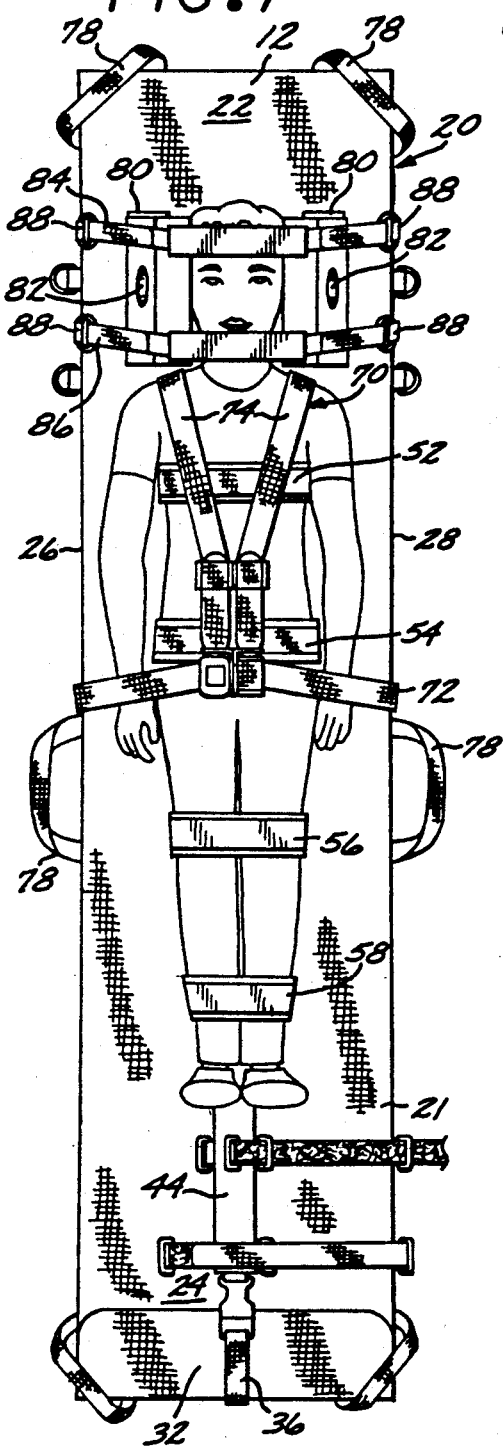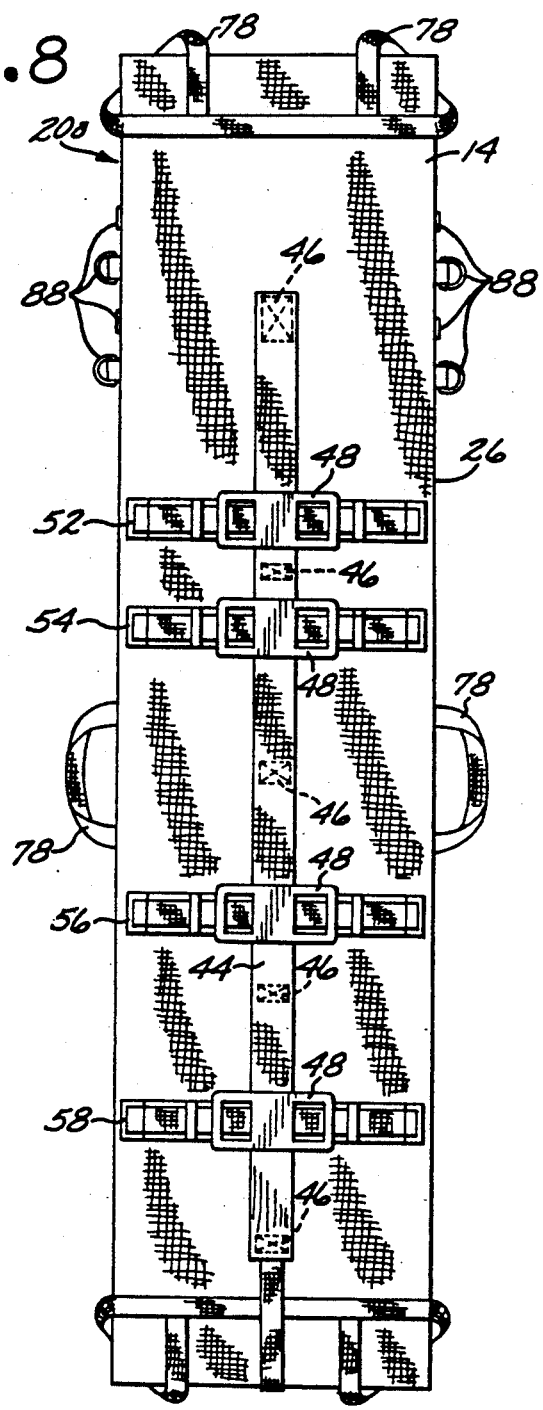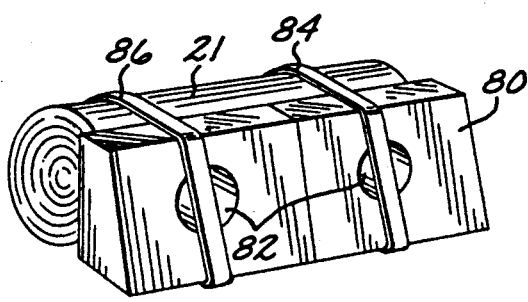

RESTRAINT STRETCHER

BACKGROUND OF THE INVENTION

1. Field of the Invention

This invention relates to a stretcher for an invalid or accident victim, and more particularly to a stretcher comprising an envelope for receiving a rigidifying backboard, and adapted to accommodate persons of various statures.

2. Description of the Prior Art

Stretchers commonly used by medical personnel for carrying and transporting sick or injured persons are not easily adjusted to accommodate persons of different sizes. The straps or other constraints should precisely overlie certain portions of the body, such as at the chest, hips, thighs and ankles. Some stretchers accomplish this by using straps or bands of constraint material wide enough to overlie, for example, the hip areas of both short and tall persons. This effectively immobilizes various sizes of injured persons but the girding material prevents access to the patient's body for administering medical treatment or for monitoring the condition of the patient.

Further, typical stretchers of the prior art comprise an elongated bag which receives a longitudinal stiffener or backboard to support the weight of the patient. The backboard has side openings or slots for lifting the stretcher, but these slots are of little use where the body of the patient is so large that the slots are covered.

A characteristic common to many prior art stretchers is the use of straps whose anchorage or attachment points are located underneath the stretcher, with the straps extending around the sides to overlie the patient. The wide backboard used for an adult locates the straps relatively far from the sides of a young child so that the transverse constraint on a child is not adequate.

Those bag-backboard designs of the prior art which utilize a plurality of girding straps generally have no means to enable individual straps to be removed and replaced should they become soiled or soaked with blood or other body fluids. Moreover, there is no padding of the board for patient comfort, presumably because this avoids soaking up of body fluids by the padding.

Many prior art strap arrangements also lack a simple and effective means to prevent longitudinal movement of a patient. This can occur during transportation, particularly on rapid deceleration of the transporting vehicle. Transverse girding straps alone are not sufficient to stop longitudinal movement.

SUMMARY OF THE INVENTION

According to the present invention, a stretcher comprising an envelope for receiving a rigidifying backboard, and is provided to receive a rigid backboard to support and immobilize a person, using transverse straps attached to a longitudinally disposed retainer strap. The retainer strap is attached to the stretcher at longitudinally spaced intervals to define loops through which the transverse straps extend. The loops are longer than the width of the straps so that the straps are longitudinally adjustable to fit both tall and short persons.

The free ends of the transverse straps are adapted to be attached together to secure a patient on the stretcher. The straps are otherwise circumferentially continuous so they can be quickly pulled out of the retainer strap loops and replaced should they become soiled or otherwise unusable. Removable anchorage brackets cooperate with the transverse straps adjacent the retainer strap to releasably constrain the transverse straps against circumferential movement to maintain them in position during normal use.

The retainer strap can be located on the upper or lower side of the stretcher according to whether the stretcher is to be used, for example, by an adult or a child. If attached to the upper side, the straps will extend from beneath a child to pass around the body of the child. Since a child is not as wide as the width of an adult stretcher, this extension of the straps along the sides of the child better constrains the child against transverse movement.

For an adult, the transverse straps would be attached to a retainer strap located on the underside of the stretcher. The straps then extend upwardly from the side edges of the stretcher, but are close enough to the sides of the adult that they positively constrain the greater weight of the adult's body against transverse movement.

The stretcher includes padding for patient comfort, and handles are located for extension outwardly of the stretcher to facilitate lifting of a stretcher occupied by a large person who substantially overlies all of the stretcher.

Shoulder harness means are provided to cooperate with a waist strap encircling the stretcher to constrain a person on the stretcher against longitudinal movement, the waist strap being circumferentially movable for properly centering the harness means along the medial plane of the stretcher.

Other objects and features of the invention will become apparent from consideration of the following description taken in connection with the accompanying drawings.

BRIEF DESCRIPTION OF THE DRAWINGS

FIG. 7 is a top plan view of the stretcher supporting a small person;

FIG 8 is a bottom plan view of a second embodiment of the stretcher adapted for use by a larger person or adult; and FIG. 9 is a perspective view showing the stretcher without any longitudinal stiffening means, rolled up and strapped to the head supports or restraints for compact storage or convenient carrying.

DETAILED DESCRIPTION OF PREFERRED EMBODIMENTS

Figure 1:
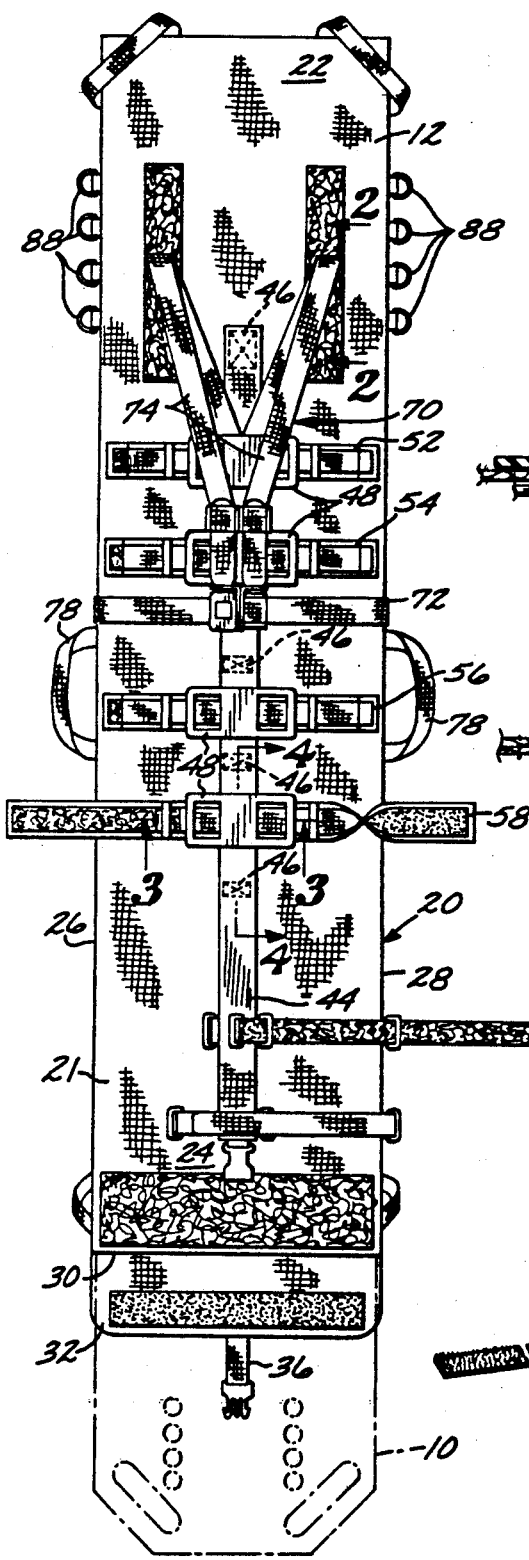
FIG. 1 is a top plan view of the stretcher as it would be used by a small person or child.
Figure 2:
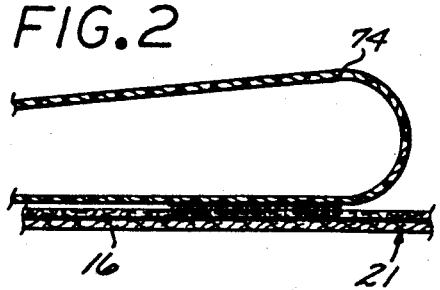
FIG. 2 is a view taken along the line 2—2 of FIG. 1.

Referring now to FIGS. 1-17, the stretcher of the present invention is generally designated 20. It is elongated and substantially rectangular in shape. The stretcher 20 includes an upper side or surface 12 upon which the patient or injured person is carried, and an underside or lower surface 14. Although the stretcher can be made so that the upper and lower surfaces are unitary, it is preferred to provide an elongated envelope or bag 21 open at one end to receive a longitudinal stiffening means or board 10. The upper and lower surfaces 12 and 14 are then defined by the bag, being joined together along their outer edges to define the side edges 26 and 28 of the stretcher.

The head portion 22 of the bag is closed, and the foot portion 24 can be opened at 30 to receive the board. It can be closed by a flap 32 through the use of fastening means such as that known by the trademark "Velcro".

The terms upper, lower, etc. correspond to the normal orientation of a person lying on the upper surface 12 of the stretcher 20.

Stretcher 20 is constructed of lightweight, flexible and waterproof material 16 that can be rolled up, as seen in FIG. 9. For patient comfort the upper side 12 of the stretcher 20 includes a padding layer to cushion the patient from the hard surface of the board 10, and also to provide thermal insulation. The padding is preferably a closed cell foam material that will not absorb moisture or blood or other body fluids.

The board 10 provides structural support for the weight of the patient's body and can be made of any suitable material or shape capable of providing this function. In one exemplary embodiment of the present invention the board 10 measured 6 feet in length, 16 inches in width, and ¾ inch in thickness. A fastening strap 36 can be attached to the underside of the bag 21, for extension around the end flap 32 to ensure retention of the board in position within the bag 21. A fastener such as a buckle 38 can be attached to the upper side of the stretcher to receive and hold the free end of the fastening strap 36.

A longitudinal retainer strap 44 is located along the medial plane of the stretcher 20 on its top surface 12, extending longitudinally from the head portion 22 to the foot portion 24. The retainer strap 44 is stitched or otherwise suitably secured to the material or fabric of the bag 21 at longitudinally spaced apart locations 46, as seen in FIG. 4, to provide a plurality of longitudinally oriented loops.

A plurality of transverse straps are disposed through the loops, including a chest strap 52, a hip strap 54, a thigh strap 56 and an ankle strap 58. The free or end portions of each lateral strap include complemental Velcro portions for attaching the free ends together and thereby secure the patient in position.

The lateral straps are narrower than the loops in the retainer strap 44 so that they can be adjusted longitudinally for positioning according to the height and size of the patient. Each of these straps is releasably secured in position by anchorage brackets 48 located in adjacent overlying relation to the retainer strap 44.

Figure 3:
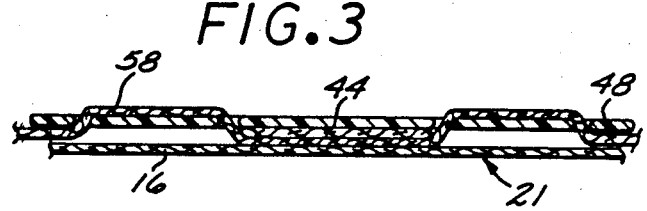
FIG. 3 is a view taken along the line 3—3 of FIG. 1.
Figure 4:
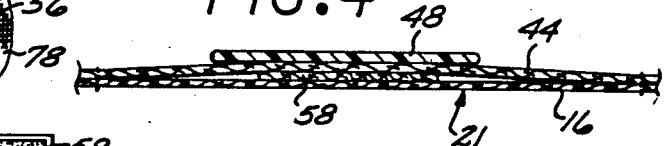
FIG. 4 is a view taken along the line 4—4 of FIG. 1.

As best seen in FIGS. 3 and 4, each anchorage bracket 48 includes four slots through which the associated transverse strap is extended in serpentine fashion to overlie the retainer strap and also engage the margins of the bracket slots to constrain the strap against unwanted circumferential movement. This arrangement allows the transverse straps and the brackets to be easily removed for cleaning and replacement when necessary. Of course, other arrangements of slots or other suitable means can be employed, if desired, for constraining the transverse strap against transverse movement relative to the anchorage bracket.

As seen in FIG. 1, the chest strap 52 overlies the upper torso area or chest of the patient. It is adjustably slidable longitudinally along the retainer strap 44 to overlie the chest of the patient It extends from under the patient at the anchoring bracket 48, wraps around the sides of the patient, and is then secured at its free ends, as previously indicated.

The arrangement of the other transverse straps is similar. The hip portion of the patient is secured by the hip strap 54, which extends outwardly from the retainer strap 44 at the medial plane of the stretcher, and then upwardly and around the body. The arrangement and function of the other transverse straps is similar, as will be apparent.

The thigh strap 56 is preferably located just above the knee caps of the patient to minimize knee flexing or other movements of the hip girdle. The ankle strap 58 offers additional restraint on the ankles to enhance immobilization of the body's lower extremities.

A torso harness 70 is provided to secure the patient against longitudinal movement and to stabilize the torso area. This is important during transportation of the patient, when the transporting vehicle might suddenly accelerate or decelerate. The torso harness 70 comprises a transverse waist strap 72 and a pair of shoulder straps 74. The waist strap slidably extends through a suitable support for enabling circumferentially adjustable movement, such as a transversely disposed, open-ended fabric envelope or sleeve (not shown) stitched or sewn integral with the underside of the bag 21. The free ends of the waist strap include complemental vehicle seat belt type portions which releasably interconnect at the waist of the patient. The circumferentially movable mounting of the waist strap enables the strap to be moved to locate the buckle portions along the medial plane of the stretcher for better engagement by the shoulder straps 74.

The shoulder straps are sewn or otherwise attached to the upper side of the stretcher at a point behind the location of the patient's back. The straps then normally extend over the patient's shoulders, and then toward the waist strap 72. The free ends of the straps 74 include fittings which are slotted to detachably receive the tongue portion of the interconnected waist strap buckle portions. This anchors the shoulder straps in position, but releases them when the waist strap buckle portions ar disconnected. The length of each shoulder strap 74 is adjustable through the use of suitable fittings which are well known in the art of vehicle restraint systems.

Handles 78 made of flexible fabric are sewn or otherwise attached to the underside of the bag 21 and extend laterally or outwardly for easy grasping by attendants.

The present stretcher also preferably includes elastic arm restraints (not shown) attached to the opposite side edges 26 and 28 of the stretcher. These are adapted to encircle the arms of the patient slightly above the wrist area. The separate provision of the arm restraints enables medical care to be given to the individual's arms and hands when necessary without any need for disconnecting any of the other stretcher straps.

In another embodiment of the present invention, the restraining strap 44 is fastened to the underside 14 of the bag 21, as seen in FIG. 8. This locates the transversely extending straps so that they bear against the side edges 26 and 28 before they overlie the patient. This is a useful arrangement for transporting adults on the stretcher. Since the adult is usually as wide as the stretcher, the sides of the patient are engaged by the straps and the patient is thereby constrained against lateral rolling or sliding. In addition, because the straps engage both of the stretcher sides, there is no tendency for an adult to roll transversely, which might occur with the location of the restraint straps in the first embodiment described.

Figure 5:
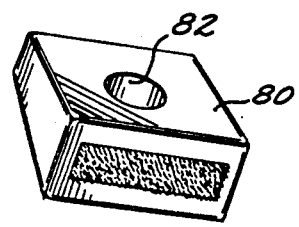
FIG. 5 is a perspective view of one of the head supports or restraints.
Figure 6:
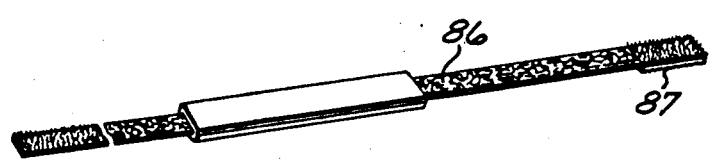
FIG. 6 is a perspective view of one of the head straps.

The stretcher 20 also includes a pair of head supports or restraints 80 made of resilient foam material or the like, as seen in FIGS. 5-7. They are adapted to be located on opposite sides of the patient's head. An opening 82 in each head restraint provides access to the ears of the patient.

The head restraints 80 are secured in position by a pair of straps 84 and 86 having fastening means 87 at their free ends which cooperate with usual "D" rings 88 attached to the side edges of the stretcher.

In operation, the stretcher 20 is placed adjacent the body of the patient with the hip strap 54 aligned with the hip of the patient. The patient is then placed on the stretcher, and all of the transverse straps are then longitudinally positioned along the retaining strap 44 so that they are properly fitted to the patient. The spacing between the straps allows easy access to most portions of the patient's body where necessary for monitoring the cardiac and respiratory functions of the patient and for rendering appropriate medical care, such as cardiopulmonary resuscitation and defibrillation procedures. This would not be possible with the wide sheet girding materials used in many other stretcher designs.

Various modifications and changes may be made with regard to the foregoing detailed description without departing from the spirit of the invention.

I claim:

1. A stretcher for mounting upon an elongated backboard for supporting and immobilizing a person, the stretcher comprising:
   an elongated envelope adapted to slidably receive enclose a rigidifying backboard, and having a longitudinal centerline and opposite side edges;
   retainer means extending longitudinally of and attached to one side of the envelope adjacent the longitudinal centerline at longitudinally spaced apart locations to define unattached sections of the retainer means; and
   a plurality of transverse straps extending through the unattached sections, respectively, the transverse straps being of lesser widths than the sections whereby the transverse straps are adjustable longitudinally for adaptation to different sized persons, the transverse straps being laterally movable in the sections for removal and replacement.

2. A stretcher according to claim 1 and further comprising:
   a waist strap for overlying a person on the stretcher;
   fastening means for releasably attaching the free ends of the waist strap; and
   a torso harness including a pair of shoulder straps each attached at one end to the envelope and adapted to pass over the shoulders and toward the waist strap, the free ends of the shoulder straps being adapted for attachment to the fastening means to constrain the person against longitudinal movement.

3. A stretcher according to claim 1 wherein the transverse straps include a chest strap, a hip strap, a thigh strap, and an ankle strap for releasably constraining the corresponding portions of the person against movement 4. A stretcher according to claim 1 wherein the transverse straps are circumferentially continuous between their free ends.

5. A stretcher according to claim 2 wherein the envelope includes holding means for supporting the waist strap for circumferential movement in order to center the fastening means at the medial plane of the envelope.

6. A stretcher according to claim 1 including a plurality of slotted anchorage brackets adjacent the retainer means for receiving, respectively, the transverse straps, each strap being reversely passed in serpentine fashion through the slots of an associated anchorage bracket to releasably constrain the transverse strap against circumferential movement.

7. A stretcher according to claim 1 which further comprises arm restraints attached to the envelope adjacent its side edges and adapted to pass around the person's arms to releasably constrain the arms against movement.

8. A stretcher according to claim 1 wherein the retainer means is attached to the upper side of the envelope for use of the stretcher by a small person whose body is significantly narrower than the stretcher.

9. A stretcher according to claim 1 wherein the retainer means is attached to the underside of the envelope for use of the stretcher by a person whose body is approximately as wide as the stretcher.

10. A stretcher according to claim 1 which further comprises head restraints detachably fixed to the envelope adjacent the side edges for engagement with the sides of the head of a person on the stretcher; and a pair of longitudinally spaced apart transverse head straps attached to the stretcher and adapted to overlie the forehead and chin areas of the head.

11. A stretcher according to claim 1 including padding carried by the envelope to underlie the person.

12. A stretcher according to claim 1 wherein carrying straps are attached to the underside of the envelope and extend outwardly of the stretcher for convenient grasping by attendants, regardless of the size of the person on the stretcher.

* * * * *

UNITED STATES PATENT AND TRADEMARK OFFICE
CERTIFICATE OF CORRECTION

PATENT NO. : 5,014,374
DATED : May 14, 1991
INVENTOR(S) : Gary R. Williams

It is certified that error appears in the above-identified patent and that said Letters Patent is hereby corrected as shown below:

Column 1, line 54, after "an" insert --elongated--;
after "envelope" delete [for receiving a rigidifying backboard, and];

Column 4, line 42, delete "ar" and insert --are--;

Column 6, line 43, delete [stretcher] and insert --envelope--.

Signed and Sealed this

Twenty-seventh Day of October, 1992

Attest:

DOUGLAS B. COMER

Attesting Officer    Acting Commissioner of Patents and Trademarks